US006448410B1

(12) United States Patent
Howarth et al.

(10) Patent No.: US 6,448,410 B1

(45) Date of Patent: Sep. 10, 2002

(54) PRODUCTION OF COMPACTED BIOCIDAL AGENT FROM PARTICULATE BIOCIDAL AGENT WITHOUT USING A BINDER

(75) Inventors: Jonathan N. Howarth; Bruce C. Peters, both of Baton Rouge, LA (US)

(73) Assignee: Albemarle Corporation, Richmond, VA (US)

(*) Notice: Subject to any disclaimer, the term of this patent is extended or adjusted under 35 U.S.C. 154(b) by 0 days.

(21) Appl. No.: 09/483,896

(22) Filed: Jan. 18, 2000

(51) Int. Cl.$^7$ .............................................. C07D 233/82

(52) U.S. Cl. .................................... 548/320.5; 424/405

(58) Field of Search ......................... 548/320.5; 424/405, 424/723; 514/389

(56) References Cited

U.S. PATENT DOCUMENTS

| | | | | |
|---|---|---|---|---|
| 2,130,805 | A | 9/1938 | Levine | 210/28 |
| 2,392,505 | A | 1/1946 | Rogers | 260/309.5 |
| 2,398,598 | A | 4/1946 | Rogers | 260/309.5 |
| 2,779,764 | A | 1/1957 | Paterson | 260/309.5 |
| 2,795,556 | A | 6/1957 | Quinn | 252/187 |
| 2,868,787 | A | 1/1959 | Paterson | 260/248 |
| 2,971,959 | A | 2/1961 | Waugh et al. | 260/309.5 |
| 2,971,960 | A | 2/1961 | Waugh et al. | 260/309.5 |
| 3,121,715 | A | 2/1964 | Waugh et al. | 260/248 |
| 3,147,259 | A | 9/1964 | Paterson | 260/248 |
| 3,345,371 | A | 10/1967 | Paterson | 260/192 |
| 4,078,099 | A | 3/1978 | Mazzola | 427/213 |
| 4,126,717 | A | 11/1978 | Mazzola | 427/220 |
| 4,136,052 | A | 1/1979 | Mazzola | 252/94 |
| 4,242,216 | A | 12/1980 | Daugherty et al. | 252/103 |
| 4,327,151 | A | 4/1982 | Mazzola | 428/407 |
| 4,427,692 | A | 1/1984 | Girard | 424/273 R |
| 4,465,839 | A | 8/1984 | Schulte et al. | 548/310 |
| 4,532,330 | A | 7/1985 | Cole | 548/311 |
| 4,537,697 | A | 8/1985 | Girard | 252/90 |
| 4,560,766 | A | 12/1985 | Girard et al. | 548/311 |
| 4,571,333 | A | 2/1986 | Hsiao et al. | 424/22 |
| 4,597,941 | A | 7/1986 | Bottom et al. | 422/37 |
| 4,621,096 | A | 11/1986 | Cole | 514/389 |
| 4,654,424 | A | 3/1987 | Girard et al. | 548/311 |
| 4,659,359 | A | 4/1987 | Lorenz et al. | 71/67 |
| 4,677,130 | A | 6/1987 | Puzig | 514/389 |
| 4,698,165 | A | 10/1987 | Theyson | 210/755 |
| 4,713,079 | A | 12/1987 | Chun et al. | 8/101 |
| 4,728,453 | A | 3/1988 | Choy | 252/91 |
| 4,745,189 | A | 5/1988 | Lee et al. | 544/221 |
| 4,803,079 | A | 2/1989 | Hsiao et al. | 424/468 |
| 4,867,895 | A | 9/1989 | Choy | 252/91 |
| 4,919,841 | A | 4/1990 | Kamel et al. | 252/186.26 |

(List continued on next page.)

FOREIGN PATENT DOCUMENTS

| | | |
|---|---|---|
| CA | 1230825 | 12/1987 |
| CA | 2042430 | 11/1991 |
| CA | 2163596 | 9/1996 |
| EP | 0177645 | 4/1986 |
| EP | 0206725 | 12/1986 |
| EP | 0228593 | 7/1987 |
| EP | 0581826 | 9/1995 |
| GB | 1054243 | 1/1967 |
| GB | 1600289 | 10/1981 |
| GB | 2273106 | 6/1994 |
| WO | 8910696 | 11/1989 |
| WO | 9630491 | 10/1996 |
| WO | 9715652 | 5/1997 |
| WO | 9720546 | 6/1997 |
| WO | 9720909 | 6/1997 |
| WO | 9743264 | 11/1997 |
| WO | 9743392 | 11/1997 |
| WO | 0034186 | 6/2000 |

OTHER PUBLICATIONS

HCAPLUS Abstract of JP 07277912 A2 issued 1995.
HCAPLUS Abstract of JP 08027119 A2 issued 1996.
HCAPLUS Abstract of JP 08239699 A2 issued 1996.
HCAPLUS Abstract of JP 09087684 A2 issued 1997.
HCAPLUS Abstract of JP 09227317 A2 issued 1997.
Corral et al., "Substitution in the Hydantoin Ring. III. Halogenation", J. Org. Chem., 1963, vol. 28, pp. 1100–1104.
Jolles, "General Methods of Bromination", Bromine and its Compounds, 1966, Ernest Benn, London, pp. 365.
Markish et al., "New Aspects on the Preparation of 1,3–Dibromo–5,5–Dimethylhydantoin", Ind. Eng. Chem. Res. 1995, vol. 34, pp. 2125–2127.
Orazi et al., "Halogenacion con 3–Bromo–5,5–Dimetil–Hidantoina", Anales Assoc. Quim. Argentina, 1949, vol. 37, pp. 192–196. (Not translated).
Orazi et al., "Halogenacion Con 1–3–Dibromo–5, 5–Dimetil–Hidantoina", Anales Assoc. Quim. Argentina, 1950, vol. 38, pp. 5–11. (Not translated).
Mar., "Advanced Organic Chem.", 1992, 4$^{th}$ Edition, pp. 639–640.
HCAPLUS Abstract of JP 07171576 A2 issued 1995.
Chowhan et al., "Hardness Increase Induced by Partial Moisture Loss in Compressed Tablets and Its Effect on In Vitro Dissolution", J. Pharm. Sciences, Oct. 1978, vol. 67, No. 10, pp. 1385–1389.
Krycer et al., "An Evaluation of Tablet Binding Agents Part II. Pressure Binders", Powder Technology, 1983, vol. 34, pp. 53–56.
Petterson, "N–Halogen Compounds. I. Decomposition of 1,3–Dichloro–5,5–dimethylhydantoin in Water at pH 9", J. Org. Chem., 1959, vol. 24, pp. 1414–1419.

*Primary Examiner*—Robert Gerstl
(74) *Attorney, Agent, or Firm*—E. E. Spielman, Jr.

(57) ABSTRACT

A shape-retentive compacted article is produced from 1,3-dibromo-5,5-dimethylhydantoin particulate solids by (a) granulating the particulate solids without use of a binder, and (b) pressure compacting granulated 1,3-dibromo-5,5-dimethylhydantoin granules formed in (a) that have a U.S. standard mesh size in the range of about 80 mesh to about 3 mesh, again without use of a binder. So far as is known, never before have 1,3-dibromo-5,5-dimethylhydantoin particulate solids been converted into a compacted form by any method.

14 Claims, No Drawings

U.S. PATENT DOCUMENTS

| | | | | |
|---|---|---|---|---|
| 4,925,866 | A | 5/1990 | Smith | 514/389 |
| 5,338,461 | A | 8/1994 | Jones | 210/755 |
| 5,339,889 | A | 8/1994 | Bigham | 165/1 |
| 5,422,126 | A | 6/1995 | Howarth et al. | 424/723 |
| 5,565,109 | A | 10/1996 | Sweeny | 210/755 |
| 5,565,576 | A | 10/1996 | Hall et al. | 548/317.1 |
| 5,578,559 | A | 11/1996 | Dolan et al. | 510/192 |
| 5,591,692 | A | 1/1997 | Jones et al. | 504/124 |
| 5,603,941 | A | 2/1997 | Farina et al. | 424/405 |
| 5,610,126 | A | 3/1997 | Barford et al. | 510/191 |
| 5,614,528 | A | 3/1997 | Jones et al. | 514/258 |
| 5,670,451 | A | 9/1997 | Jones et al. | 504/134 |
| 5,750,061 | A | 5/1998 | Farina et al. | 264/117 |
| 5,756,440 | A | 5/1998 | Watanabe et al. | 510/191 |
| 5,763,376 | A | 6/1998 | Ward et al. | 510/191 |
| 5,780,641 | A | 7/1998 | Yerushalmi et al. | 548/320.5 |
| 5,859,060 | A | 1/1999 | Platt | 514/569 |
| 5,942,153 | A | 8/1999 | Heydel | 252/187.33 |
| 5,958,853 | A | 9/1999 | Watanabe | 510/192 |
| 5,972,864 | A | 10/1999 | Counts | 510/192 |
| 5,981,461 | A | 11/1999 | Counts et al. | 510/365 |

PRODUCTION OF COMPACTED BIOCIDAL AGENT FROM PARTICULATE BIOCIDAL AGENT WITHOUT USING A BINDER

REFERENCE TO OTHER APPLICATIONS

Commonly-owned copending application Ser. No. 09/484,844, filed Jan. 18, 2000, by one of us and some of our colleagues, describes and claims chemical processes for producing, inter alia, 1,3-dibromo-5,5-dimethylhydantoin in the form of particulate solids which can be pressure-compacted without use of a binder. Commonly-owned copending application Ser. No. 09/484,687, filed Jan. 18, 2000, by us and some of our colleagues, describes and claims 1,3-dibromo-5,5-dimethylhydantoin particulate solids producible by the processes of application Ser. No. 09/484,844, such solids having unprecedented enhanced properties, and compacted articles made from such particulate solids without use of a binder. Commonly-owned copending application Ser. No. 09/487,816, filed Jan. 18, 2000, by us relates in part to converting 1,3-dihalo-5,5-dimethylhydantoins into compacted articles using novel binders. Commonly-owned copending application Ser. No. 09/484,938, filed Jan. 18, 2000, by one of us and some of our colleagues, describes and claims methods for effecting efficacious microbiological control utilizing 1,3-dibromo-5,5-dimethylhydantoin in novel compacted or non-compacted forms. Commonly-owned copending application Ser. No. 09/484,891, filed Jan. 18, 2000, by one of us relates to the compacting of 1,3-dihalo-5,5- dimethylhydantoins other than 1,3-dibromo-5,5-dimethyl-hydantoin without use of binders, and to the novel compacted forms so produced.

BACKGROUND 1,3-Dibromo-5,5-dimethylhydantoin has been produced commercially. The product, as produced and sold, is in the form of a fine powder. Its principal use is as source of bromine in conducting bromination reactions in chemical syntheses.

Widely used as a biocidal agent for water are N,N'-bromochloro-5,5-dialkylhydantoins. One of the features emphasized for such materials is that in use, the chlorine released from the biocide regenerates active bromine from inactive bromide species formed during the water treatment operation. In other words, the chlorine atom in the initial N,N'-bromochloro-5,5-dialkylhydantoin is in effect regarded as a precursor for additional active bromine for sanitation purposes.

As is well known in the art, a deficiency of chlorine, of hypochlorites, and of certain halogenated organic water-treating agents is the formation during usage of undesirable disinfection by-products. These by-products are undesirable both from the standpoint of environmental concerns and also from the standpoint of toxicological considerations.

Although 1,3-dibromo-5,5-dimethylhydantoin is referred to in patent disclosures as one of a group of biocidal agents for water treatment, so far as is known, this compound in its pure or concentrated state has never achieved commercial use as a biocide in water treatment. Instead, in the prior art, only when in admixture with much larger quantities of N,N'-bromochloro-5,5-dimethylhydantoin was 1,3-dibromo-5,5-dimethylhydantoin deemed suitable for use in water sanitation.

SUMMARY OF THE INVENTION

This invention is based on several new discoveries. First of all, one of us and some of our colleagues have discovered unexpectedly that 1,3-dibromo-5,5-dimethylhydantoin when used in treating water achieves the requirements of the U.S. Environmental Protection Agency at a dosage level that is only one-half of that required when using one or a mixture of N,N'-bromochloro-5,5-dialkylhydantoins. This discovery enables the use of extremely small concentrations of the 1,3-dibromo-5,5-dimethylhydantoin to effectively sanitize water while at the same time achieving excellent microbiological control. Further, the ability to effectively utilize such small concentrations is expected to result in significant reduction in formation of disinfection by-products.

Moreover, it has also been discovered that 1,3-dibromo-5,5-dimethylhydantoin is also highly effective in combating biofilms which are microbiological slimes that form and prosper on surfaces in industrial and recreational water systems.

Such surprising and highly beneficial discoveries are more fully described in commonly-owned application Ser. No. 09/484,938 referred to above.

This invention involves, in part, the discovery was that samples of commercially-produced 1,3-dibromo-5,5-dimethylhydantoin particulate solids obtained from three different commercial sources could not be pressure compacted into shape-retentive tablets without use of a binder. All attempts to produce tablets without use of a binder resulted in utter failure—the compacted particles delaminated and broke into pieces during extraction from the die. Thus the commercially-produced 1,3-dibromo-5,5-dimethylhydantoin particulate solids could not be converted into tablets or briquettes, which are forms in which water treating biocides are commonly used, without first mixing the commercially-produced 1,3-dibromo-5,5-dimethylhydantoin particulate solids with a binding agent, commonly referred to as a binder.

Pursuant to this invention it has been further discovered, inter alia, that it is indeed possible to produce compacted forms of non-compactible 1,3-dibromo-5,5-dimethylhydantoin particulate solids without use of a binder. This can be accomplished by granulating non-compactible 1,3-dibromo-5,5-dimethylhydantoin particulate solids without use of a binder, and pressure compacting the granulated 1,3-dibromo-5,5-dimethylhydantoin, again without use of a binder.

Another embodiment of this invention is the provision of compacted articles such as granules, tablets, briquettes, and pucks produced, without use of a binder, using a process of this invention. In preferred forms, such articles have a crush strength of at least 15 pounds per inch, and typically in the range of 15 to 70 pounds per inch of thickness.

These and other embodiments and features of this invention will be still further apparent from the ensuing description and appended claims.

FURTHER DETAILED DESCRIPTION OF THIS INVENTION

For ease of reference, the term "non-compactible" is used herein to denote that the given 1,3-dibromo-5,5-dimethylhydantoin particulate solids referred to cannot, without prior treatment to enhance its compactibility, be successfully converted into a shape-retentive tablet when subjected to the following conditions:

1) A 0.71 inch diameter circular die fabricated from Hastelloy® C alloy is lightly dusted with micronized polypropylene wax (MICROPRO 400 wax; Micro Powders, Incorporated, Tarrytown N.Y., or equivalent if MICROPRO 400 wax is not available).

2) A representative five-gram sample of the given 1,3-dibromo-5,5-dimethylhydantoin is manually placed into the above die.

3) The five-gram sample is pressure compacted in the die at 5000 psi using a Sintech® press (MTS Systems Corporation, Edenprairie, Minn.) equipped with a punch fabricated from Hastelloy® C alloy to form a 0.71-inch diameter circular tablet. No dwell time is used, i.e., the pressure is released just as soon as the pressure reaches 5000 psi.

4) If delamination or breakage occurs when the tablet is released from the die, the given 1,3-dibromo-5,5-dimethylhydantoin is deemed "non-compactible ".

Conversely, the term "compactible" means that the 1,3-dibromo-5,5-dimethylhydantoin particulate solids referred to can be successfully converted into a shape-retentive tablet under the conditions just described in the immediately preceding paragraph.

This invention is applicable to both compactible and non-compactible 1,3-dibromo5,5-dimethylhydantoin. However, generally speaking it is preferred to utilize this invention with non-compactible 1,3-dibromo-5,5-dimethylhydantoin, since so far as is known, there is no other way of pressure compacting non-compactible 1,3-dibromo-5,5-dimethylhydantoin into a shape-retentive article in a die without use of a binder.

A preferred process of this invention comprises the following steps:

a) compressing compactible or, preferably, non-compactible 1,3-dibromo-5,5-dimethylhydantoin particulate solids in the absence of a binder into a sheet of a thickness in the range of about 1/16 inch and about ½ inch;

b) subdividing such sheet into particles comprising particles in the range of about 80 mesh to about 3 U.S. standard mesh size, and preferably in the range of about 30 mesh to about 8 U.S. standard mesh size;

c) pressure compacting particles from b) in the range of about 80 mesh to about 3 U.S. standard mesh size, preferably particles in the range of about 30 mesh to about 8 U.S. standard mesh size, in a die in the absence of a binder mixed therewith.

Compression in a) can be conducted in any suitable press capable of applying suitable compression pressure, which typically is in the range of about 1000 to about 30,000 psi, and preferably in the ranger of about 5000 to about 25,000 psi. Preferred apparatus for such compression is a set of compression rolls. The resultant compressed shape, typically in the form of a sheet or other suitable breakable form, is then broken up into small granules in a suitable apparatus, such as, for example, in a Chilsonator® breaker (The Fitzpatrick Company, Elmhurst, Ill.). The particles in the size ranges referred to in b) are regarded as granulated 1,3-dibromo-5,5-dimethylhydantoin: If in b) particles are also formed that are larger and/or smaller than the selected size referred to in b), it is preferred to classify the particles formed in b) into (1) a fraction containing the particles in the selected size range of b), and (2) either or both of (i) a fraction composed of the larger particles, and/or (ii) a fraction composed of the smaller particles, as the case may be. Where a fraction of (i) exists, such fraction is preferably recycled to b). Where a fraction of (ii) exists, such fraction is preferably recycled to a).

If desired, the surfaces of the die used in c) may be lubricated with a suitable lubricant to facilitate removal of the compacted article from the die. However, as noted, no binder is used in this operation or for that matter, none is used in step a) either.

The time period during which the pressure is applied to the 1,3-dibromo-5,5-dimethylhydantoin solids in a) and in c) is not critical. As long as suitable compaction is achieved, the time of compaction is of little or no consequence. In any situation where the optimum time has not been previously determined, a few simple preliminary tests should readily enable such pressure conditions, including pressure times, to be determined and optimized.

The compaction or compression steps in a) and c) above are typically initiated with the 1,3-dibromo-5,5-dimethylhydantoin solids at room temperature. However, if desired, the solids can be preheated or precooled such that the compaction or compression is initiated at a temperature in the range of about 5 to about 80° C.

If desired, the 1,3-dibromo-5,5-dimethylhydantoin particulate solids can be formulated with suitable excipients such as disintegrants, lubricants, and mold release agents. Other optional ingredients which may be used in the formulation of products from the 1,3-dibromo-5,5-dimethylhydantoin particulate solids include fragrances, stabilizers, corrosion inhibitors, dyes, other biocidal agents, surfactants, effervescents, diluents, builders, chelating agents, and the like. Such ancillary materials should of course be compatible with 1,3-dibromo-5,5-dimethylhydantoin and not interfere in any material way with the excellent performance characteristics of the 1,3-dibromo-5,5-dimethylhydantoin particulate solids of this invention. The amount(s) of such ancillary materials used should of course be sufficient to serve the purpose for which it is, or they are, being used. At the same time, the amount used should not materially detract from the physical, mechanical, or performance properties of the formulated product.

Example 1 illustrates background discoveries dealt with more fully in commonly-owned copending application Ser. No. 09/484,891, referred to above. One such discovery is that 1,3-dichloro-5,5-dimethylhydantoin and N,N'-bromochloro-5,5-dimethylhydantoin particulate solids can be pressure compacted into shape-retentive tablets without use of a binder. Another such discovery is that samples of commercially-available 1,3-dibromo-5,5-dimethylhydantoin obtained from three different producers could not be pressure compacted into shape-retentive tablets without use of a binder.

EXAMPLE 1

Five-gram samples of 1,3-dibromo-5,5-dimethylhydantoin products obtained from three separate commercial sources were compacted without binder in a Sintech® press (MTS Systems Corporation, Edenprairie, Minn.) equipped with a punch and die fabricated from Hastelloy® C alloy. Before compaction the interior of the tooling surfaces were lightly dusted with a micronized wax to facilitate release of tablets from the mold. The pressure applied was 5000 psi with no dwell time. Three samples of each commercial product were subjected to these compression tests. For comparison, four-gram samples of 1,3-dichloro-5,5-dimethylhydantoin and of N,N'-bromochloro-5,5-dimethylhydantoin as received were tested in the same manner without use of a binder. It was found that shape-retentive tablets of 1,3-dibromo-5,5-dimethylhydantoin could not be produced under these conditions, whereas the two other 1,3-dihalo-5,5-dimethylhydantoin products were successfully tableted under the same conditions. The tablets formed from the 1,3-dichloro-5,5-dimethylhydantoin and from the N,N'-bromochloro-5,5-dimethylhydantoin after removal from the die were aged for 6 days at room temperature. Thereupon the tablets were subjected to crush strength testing utilizing a Sintech® 1/S compression apparatus (MTS Systems Corporation, Edenprairie, Minn.) equipped with Testworks software, which software is installed in the 1/S compression apparatus as supplied by MTS Systems Corporation. The apparatus includes a horizontal circular-shaped load cell interfaced with a computer, a digital micrometer also interfaced with the computer, and a vertical screw-driven piston that is disposed above the load cell and adapted to apply a downward force perpendicular to the load cell. The procedure for measuring crush strength involves measuring the thickness of the tablet with the micrometer to provide a digitized input to the computer. Next the tablet is placed on its edge on the load cell with the piston in contact with the upper edge of the tablet. Then the apparatus is activated whereby the piston commences applying a progressively increasing downward diametral force to the tablet. At the same time, the load cell continuously measures the downward force being applied to the tablet, and the input of such measurements is transmitted to the computer. When the force being applied reaches the point where the amount of force suddenly decreases to 10% of the immediately preceding force, the tablet has reached the breaking point, and the application of the force is immediately terminated by the software program. From the inputs to the computer, two values are provided, namely the pounds of force at the breaking point of the tablet, and the pounds of force per inch thickness of the tablet at the breaking point. Thus the greater the force applied, the greater the crush strength. Table 1 lists the average particle sizes and particle size distributions of the five commercial products as received. In those cases where it was possible to form a tablet, Table 1 also provides the results of the crush strength tests on such tablets. For convenience, the following abbreviations are used in Table 1: DBDMH is 1,3-dibromo-5,5-dimethylhydantoin, DCDMH is 1,3-dichloro-5,5-dimethylhydantoin, and BCDMH is N,N'-bromochloro-5,5-dimethylhydantoin.

late solids of the type that are not amenable to successful one-step pressure compaction into shape-retentive articles such as tablets without use of a binder; can be converted into shape-retentive articles such as tablets without use of a binder if a compaction process pursuant to this invention is used.

EXAMPLE 2

A sample of commercially-produced 1,3-dibromo-5,5-dimethylhydantoin (Albemarle Corporation), having an average particle size of about 64.5 μ, is compressed into sheet form in a continuous fashion by means of a proprietary MS-75 compactor system (Hosokawa Bepex, Minneapolis, Minn.). Five-gram samples of 1,3-dibromo-5,5-dimethylhydantoin in the range of 8 to 30 mesh size are compacted without binder in a Sintech® press (MTS Systems Corporation, Edenprairie, Minn.) equipped with a punch and die fabricated from Hastelloy® C alloy. Before manually filling the die, the interior surfaces of the die are lightly dusted with a micronized polypropylene wax (MICROPRO 400 wax; Micro Powders, Incorporated, Tarrytown, N.Y.). The pressure applied is 5000 psi with no dwell time, i.e., the pressure is released as soon as the increasing pressure reaches 5000 psi. In an operation conducted in this general manner, intact tablets with the appearance of some friability at the ridges were obtained. The tablets were aged for 6 days at room temperature. Thereupon the tablets were subjected to crush strength testing utilizing the apparatus and procedure for crush strength measurements as described in Example 1 above. In duplicate determinations, the tablets were found to have an average crush strength in the diametral direction averaging 28 pounds per inch.

As used herein, including the claims, values given for crush strength are as measured using the apparatus and procedure as described in Example 1 above. When the compacted article is in a form other than a cylindrical tablet, the article being tested is to be positioned on the load cell and under the screw-driven piston with the longest axis of the article in the vertical position. In addition, the micrometer is used to measure the thickest portion of the article when the article is positioned on the load cell and under the screw-driven piston with the longest axis of the article in the vertical position.

TABLE 1

| Particle Size | DCDMH - Aldrich | BCDMH - Aldrich | DBDMH - Aldrich | DBDMH - Albemarle | DBDMH - Great Lakes |
|---|---|---|---|---|---|
| Average | 108.1 μ | 323.8 μ | 162.1 μ | 64.59 μ | 45.23 μ |
| 10% is greater than | 195.3 μ | 877.9 μ | 359.2 μ | 162.7 μ | 78.76 μ |
| 25% is greater than | 134.4 μ | 409.9 μ | 177.6 μ | 90.12 μ | 49.76 μ |
| 50% is greater than | 80.07 μ | 173.9 μ | 86.03 μ | 39.21 μ | 34.68 μ |
| 75% is greater than | 45.99 μ | 65.39 μ | 47.37 μ | 26.85 μ | 23.25 μ |
| 90% is greater than | 27.19 μ | 29.35 μ | 27.67 μ | 17.91 μ | 13.90 μ |
| Range | 0.04–>2000 μ | 0.04–>2000 μ | 0.04–>2000 μ | 0.04–309.6 μ | 0.04–409.6 μ |
| Compaction | Intact tablets | Intact tablets | Delaminated; broken tablets | Delaminated; broken tablets | Delaminated; broken tablets |
| Crush strength lb/in | 183.6 | 83.9 | Test not possible | Test not possible | Test not possible |

It can be seen from Example 1 that the compaction characteristics of the prior commercially-available 1,3-dibromo-5,5-dimethylhydantoin are vastly different from the compaction characteristics of the prior commercially-available 1,3-dichloro-5,5-ditmethylhydantoin and N,N'-dichloro-5,5-dimethylhydantoin.

Example 2 illustrates the discovery, pursuant to this invention, that despite its vastly different compaction characteristics, 1,3-dibromo-5,5-dimethylhydantoin particu- Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent, publication, or commonly-owned patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A method of producing a shape-retentive compacted article from 1,3-dibromo-5,5-dimethylhydantoin particulate solids, which method comprises:

a) granulating 1,3-dibromo-5,5-dimethylhydantoin particulate solids without use of a binder, and b) pressure compacting granulated 1,3-dibromo-5,5-dimethylhydantoin granules formed in a) that have a U.S. standard mesh size in the range of about 80 mesh to about 3 mesh, again without use of a binder.

2. A method of claim 1 wherein said 1,3-dibromo-5,5-dimethylhydantoin particulate solids used in a) cannot be successfully converted without granulation as in a) into a shape-retentive tablet that does not delaminate or break when released from the die in a procedure in which a five-gram sample of such solids is manually placed into a die of Hastelloy C alloy that has been lightly dusted with micronized polypropylene wax, and is pressure compacted in the die at 5000 psi into a 0.71-inch diameter circular tablet, with no dwell time.

3. A method of producing a shape-retentive compacted article from 1,3-dibromo-5,5-dimethylhydantoin particulate solids, which method comprises:

a) compressing 1,3-dibromo-5,5-dimethylhydantoin particulate solids in the absence of a binder into a sheet of a thickness in the range of about 1/16 inch to about ½ inch;

b) subdividing such sheet into particles comprising particles in the range of about 80 mesh to about 3 U.S. standard mesh size; and c) pressure compacting particles from b) in the range of about 80 mesh to about 3 U.S. standard mesh size in a die in the absence of a binder mixed therewith.

4. A method of claim 3 wherein said particles in b) and in c) are in the range of about 30 mesh to about 8 U.S. standard mesh size.

5. A method of claim 3 or 4 wherein the compression in a) is conducted with the application of compression pressure in the range of about 1000 to about 30,000 psi.

6. A method of claim 3 or 4 wherein the compression in a) is conducted with the application of compression pressure in a set of compression rolls in the range of about 5000 to about 25,000 psi.

7. A method of claim 3 or 4 wherein the particles formed in b) are classified into (1) a fraction containing the particles in the size range of b), and (2) either or both of (i) and (ii), where (i) is a fraction composed of the larger particles, and (ii) is a fraction composed of the smaller particles.

8. A method of claim 7 where a fraction of (i) if it exists, is recycled to b), and a fraction of (ii) if it exists, is recycled to a).

9. A pressure compacted article formed from non-compactible 1,3-dibromo-5,5-dimethylhydantoin without use of any binder, said article produced by a method comprising:

a) granulating 1,3-dibromo-5,5-dimethylhydantoin particulate solids without use of a binder, and b) pressure compacting granulated 1,3-dibromo-5,5-dimethylhydantoin granules formed in a) that have a U.S. standard mesh size in the range of about 80 mesh to about 3 mesh, again without use of a binder.

10. A pressure compacted article formed from non-compactible 1,3-dibromo-5,5-dimethylhydantoin without use of any binder, said article produced by a method comprising:

a) compressing 1,3-dibromo-5,5-dimethylhydantoin particulate solids in the absence of a binder into a sheet of a thickness in the range of about 1/16 inch to about ½ inch;

b) subdividing such sheet into particles comprising particles in the range of about 80 mesh to about 3 U.S. standard mesh size; and c) pressure compacting particles from b) in the range of about 80 mesh to about 3 U.S. standard mesh size in a die in the absence of a binder mixed therewith.

11. An article of claim 10 wherein said particles in b) and in c) are in the range of about 30 mesh to about 8 U.S. standard mesh size.

12. An article of claim 10 wherein the compression in a) is conducted with the application of compression pressure in the range of about 1000 to about 30,000 psi.

13. An article of claim 10 wherein the compression in a) is conducted with the application of compression pressure in a set of compression rolls in the range of about 5000 to about 25,000 psi.

14. A pressure compacted article of any of claims 9–13 inclusive, having a crush strength in the range of about 15 to about 70 pounds per inch of thickness.

* * * * *